(12) United States Patent
Atta et al.

(10) Patent No.: US 9,347,114 B1
(45) Date of Patent: May 24, 2016

(54) METHOD OF SYNTHESIZING SILVER NANOPARTICLES FROM WASTE FILM

(71) Applicant: KING SAUD UNIVERSITY, Riyadh (SA)

(72) Inventors: Ayman Mohamamdy Atta, Riyadh (SA); Hamad Abdullha Al-Lohedan, Riyadh (SA); Abdelrahman Osama Ezzat, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 14/874,281

(22) Filed: Oct. 2, 2015

(51) Int. Cl.

| | |
|---|---|
| *A61K 33/38* | (2006.01) |
| *C22B 3/00* | (2006.01) |
| *C09K 15/00* | (2006.01) |
| *A01N 59/16* | (2006.01) |
| *A61K 9/51* | (2006.01) |
| *C22B 3/22* | (2006.01) |
| *C23F 11/00* | (2006.01) |
| *A61K 47/02* | (2006.01) |

(52) U.S. Cl.
CPC .............. *C22B 11/046* (2013.01); *A01N 59/16* (2013.01); *A61K 9/5192* (2013.01); *A61K 33/38* (2013.01); *A61K 47/02* (2013.01); *C09K 15/00* (2013.01); *C22B 3/22* (2013.01); *C23F 11/00* (2013.01)

(58) Field of Classification Search
None
See application file for complete search history.

(56) References Cited

U.S. PATENT DOCUMENTS

| | | | | |
|---|---|---|---|---|
| 4,078,916 A | * | 3/1978 | Gerber ..................... | C08J 3/14 134/13 |
| 4,324,705 A | * | 4/1982 | Seto ........................ | B29B 17/02 134/10 |
| 4,612,057 A | * | 9/1986 | Buser ..................... | C22B 11/025 134/13 |
| 5,017,468 A | * | 5/1991 | Joly ....................... | G03C 1/015 430/567 |

OTHER PUBLICATIONS

Nakiboğlu et al.; Turk J Chem; 25 (2001); pp. 349-353.*
Shankar et al.; Mater. Express.; vol. 5, No. 2; p. 165 (2015).*
Rauwel et al.; Advances in Materials Science and Engineering; vol. 2015, pp. 1-9 (2015).*
SciFinder NPL search results; 2 pages; downloaded Jan. 28, 2016.*
Google NPL Search results; downloaded Jan. 28, 2016.*
Google Scholar NPL search results; downloaded Jan. 28, 2016.*
Nakiboğlu et al., "*A Novel Silver Recovery Method from Waste Photographic films with NaOH Stripping.*" Turk J. Chem., 2003, 27, pp. 127-133.

* cited by examiner

*Primary Examiner* — Jeffrey T Palenik
(74) *Attorney, Agent, or Firm* — Richard C. Litman

(57) ABSTRACT

A method of synthesizing silver nanoparticles from waste film includes providing waste film including a silver halide salt and gelatin, mixing the waste film with an alkaline solution to form a mixture, heating the mixture, and subjecting the mixture to ultracentrifugation to isolate silver nanoparticles in the mixture. The film can include waste radiographic or photographic film pieces. Glucose and/or polyvinylpyrrolidone (PVP) may be added to the mixture. The nanoparticles can have an average particle size of about 2 nm to about 10 nm. The silver nanoparticles can be resistant to synthetic stomach fluid and showed high antimicrobial activity.

20 Claims, 10 Drawing Sheets

METHOD OF SYNTHESIZING SILVER NANOPARTICLES FROM WASTE FILM

BACKGROUND OF THE INVENTION

1. Field of the Invention

The present invention relates to the synthesis of silver nanoparticles, and particularly to synthesis of highly dispersed silver nanoparticles recovered from photographic and X-ray medical film waste.

2. Description of the Related Art

Because of their unique properties (e.g., size and shape depending upon optical, electrical, and magnetic properties), silver nanoparticles can be useful in antimicrobial applications, biosensor materials, composite fibers, cryogenic superconducting materials, cosmetic products, and electronic components. Several physical and chemical methods have been used for synthesizing and stabilizing silver nanoparticles. Conventional methods for producing silver nanoparticles from silver chloride, however, typically require use of toxic reducing agents.

Silver is the reflective coating of choice for solar reflectors, and X-ray films used in medicine and photographic plates. Around 18-20% of the world's silver needs are supplied by recycling photographic waste. It has been reported that 25% of the world's silver needs are supplied by recycling, out of which 75% is obtained. Thus, X-ray films can serve as a secondary source for recycled silver.

Various methods have been utilized in the recovery of silver from X-ray films, which include adsorption of silver from synthetic photographic and spent fix solutions on granulated activated carbon in a batch process; industrial enzymatic process for the recovery of silver and poly(ethylene terephthalate) (PET) from used lithe film for printing; spent fixing bath; using a constructed pilot reactor with a protease from an alkalophile; and recovery of silver from X-ray film processing effluents by precipitation. Silver recovered from X-ray films by dissolving the silver compounds with concentrated nitric acid showed that a very high quantity of silver can be recovered. Silver has also been recovered from photographic processing solution by replacing the silver with another metal such as zinc by electrolysis or by chemical precipitation with sulphide. Silver is then recovered from silver residue. However, stripping the gelatin-silver layer by conventional methods can cause environmental hazards, are time consuming, or are very expensive.

Thus, a method of synthesizing silver nanoparticles using film waste solving the aforementioned problems is desired.

SUMMARY OF THE INVENTION

A method of synthesizing silver nanoparticles from waste film can include providing waste film including a silver halide salt and gelatin, mixing the waste film with a sodium hydroxide solution or an ammonia solution to form a mixture, heating the mixture, and subjecting the mixture to ultracentrifugation to isolate silver nanoparticles in the mixture. The mixture may be heated to temperatures of about 50° C. to about 70° C. The film can include waste radiographic or photographic film pieces. The radiographic film can be medical X-ray film. Glucose and/or polyvinylpyrrolidone (PVP) may be included in the mixture. The nanoparticles can have an average particle size of about 2 nm to about 10 nm. The silver nanoparticles produced by the present methods can be monodisperse and can be resistant to synthetic stomach fluid.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
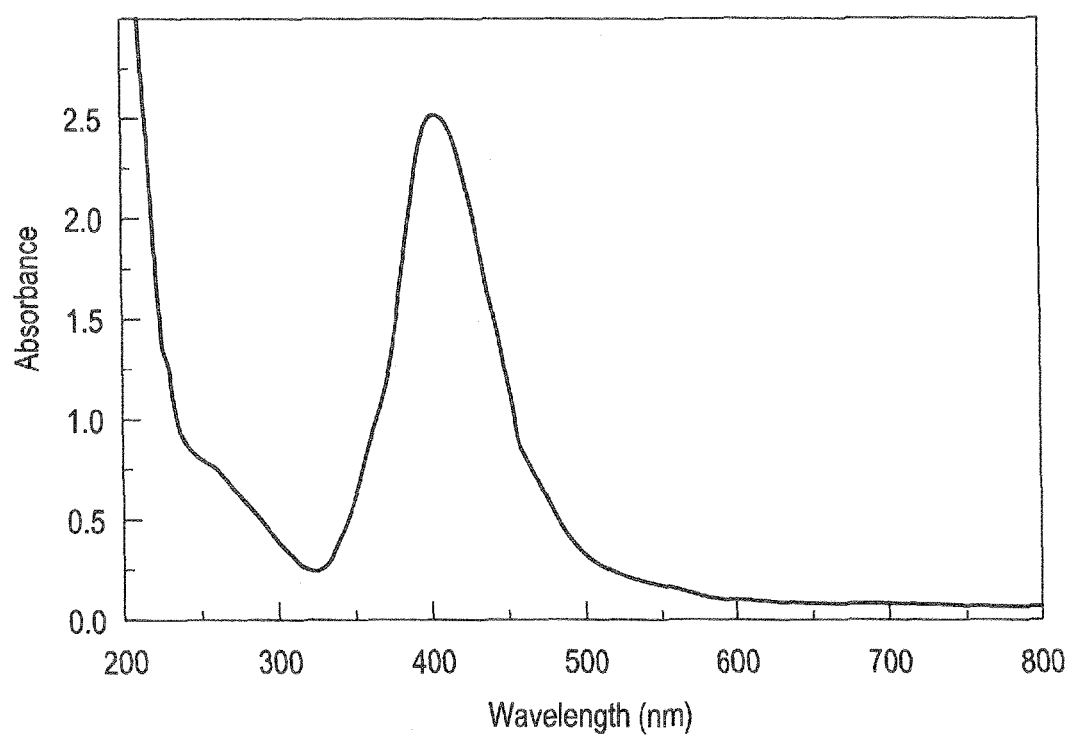
FIG. 1 shows the UV-Vis spectrum of product obtained by the method of Example 2.

A method of synthesizing silver nanoparticles from waste film can include providing waste film including a silver halide salt and gelatin, mixing the waste film with an alkaline solution to form a mixture, heating the mixture, and subjecting the mixture to ultracentrifugation to isolate silver nanoparticles in the mixture. The mixture can be heated to temperatures of about 50° C. to about 70° C. The film can include waste radiographic or photographic film pieces. The radiographic film can be medical X-ray film. The alkaline solution can be a sodium hydroxide solution or an ammonia solution. Glucose and/or polyvinylpyrrolidone (PVP) may be included in the mixture. Glucose, as an aldehyde, can reduce silver cations to silver atoms and can be oxidized to gluconic acid. The nanoparticles can have an average particle size of about 2 nm to about 10 nm. The silver nanoparticles produced by the present methods can be monodisperse, resistant to synthetic stomach fluid, and inhibit corrosion for steel in aqueous acid solution. The silver nanoparticles prepared by the present methods have high antimicrobial activity at low concentrations.

As defined herein, the term "nanoparticles" are particles between 1 and 100 nanometers in size. The term "photographic film" is a strip or sheet of transparent plastic film base coated on one side with a gelatin emulsion containing microscopically small, light-sensitive silver halide crystals. The sizes and other characteristics of the crystals determine the sensitivity, contrast, and resolution of the film. For black-andwhite photographic film, there is usually one layer of silver salts. When the exposed grains are developed, the silver salts are converted to metallic silver, which blocks light and appears as the black part of the film negative. The color film uses at least three layers. Dyes, which adsorb to the surface of the silver salts, make the crystals sensitive to different colors. Typically the blue-sensitive layer is on top, followed by the green and red layers. During development, the exposed silver salts are converted to metallic silver, just as with black-and-white film. But in a color film, the by-products of the development reaction simultaneously combine with chemicals known as color couplers that are included either in the film itself or in the developer solution to form colored dyes. Because the by-products are created in direct proportion to the amount of exposure and development, the dye clouds formed are also in proportion to the exposure and development. Following development, the silver is converted back to silver salts in the bleach step. It is removed from the film in the fix step. This leaves behind only the formed color dyes, which combine to make up the colored visible image.

Photographic emulsion is a light-sensitive colloid. Most commonly, in silver-gelatin photography it consists of silver halide crystals dispersed in gelatin. Photographic emulsion is not a true emulsion, but a suspension of solid particles (silver halide) in a fluid (gelatin in solution). Gelatin is a mixture of peptides and proteins produced by partial hydrolysis of collagen extracted from the skin, bones, and connective tissues of animals. Photographic and pharma grades of gelatin are generally made from beef bones.

Silver nanoparticles can be prepared from a silver halide salt, e.g., silver chloride (AgCl) using the methods described herein. The present inventors have discovered that gelatin present in photographic and radiographic films can reduce a silver halide salt, e.g., AgCl, at low temperatures in the presence of an alkaline medium, such as a NaOH or ammonia solution. The present methods provide a simple "green" or environmentally friendly route for producing silver nanoparticles by reducing silver chloride using gelatin of photographic and medical X-ray films in alkali media. Glucose can be used to control silver nanoparticle size and stability. The present methods unexpectedly provide highly disperse silver nanoparticles with high yield without the use of an external reducing agent based on toxic agents.

Transmission electron microscopy (TEM), dynamic light scattering (DLS) and UV-Vis spectroscopy were employed to characterize the silver nanoparticles prepared according to the present methods. In the UV-Vis spectra (FIGS. 1-3), the silver nanoparticles display a surface plasmon resonance (SPR) band at around 400 nm. The small shift to the left (blue-shift) or to the right (red-shift) in the wavelengths ($\lambda_{max}$) of the SPR peak can be attributed to the production of silver nanoparticles mixed with silver oxide ($Ag_2O$) at various shapes or sizes of formed silver nanoparticles. On the other hand, the intensity of the SPR peak indicates the continued reduction of the silver ions. Additionally, the increase of the absorbance at the same silver nanoparticle concentration indicates the increased concentration and yield of silver nanoparticles. For example, a surface plasmon resonance (SPR) of about 405 nm indicated the formation of the silver nanoparticles. UV-vis spectra indicated that ammonia cannot form silver nanoparticles, while NaOH succeeded to produce silver nanoparticles. The present methods demonstrated successful synthesis of silver nanoparticles with an average particle size of about 2-10 nm.

TEM results represented in FIGS. 4-9 indicated that the samples obtained in glucose and glucose/PVP solutions retained a narrower particle size distribution. In particular, the particle size of silver nanoparticles obtained in glucose/PVP solutions using NaOH is smaller than in the glucose solutions, which can be related to rate of reduction reaction. The methods described in Examples 3 and 4 below used glucose as a reducing agent for silver halide salt. The methods described in Examples 5 and 6 below used PVP as a stabilizer besides using glucose as a reducing agent. The method described in Example 6 below produced monodisperse silver nanoparticles. Additionally, the silver nanoparticles showed good resistance to stomach synthetic fluid, which is at 0.5 M HCl.

The present method of producing silver nanoparticles does not require use of any toxic reducing agent. The silver nanoparticles formed can be monodisperse or have a narrow particle size distribution. The particle size can be about 10 nm or less. The silver nanoparticles can have strong stability in an aqueous acidic solution. The present methods can convert silver chloride into silver nanoparticles using an alkaline solution, such as a sodium hydroxide solution, as provided in chemical Equation 1:

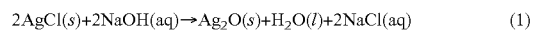

$$2AgCl(s) + 2NaOH(aq) \rightarrow Ag_2O(s) + H_2O(l) + 2NaCl(aq) \quad (1)$$

As demonstrated in the examples below, the gelatin released from the photographic or radiographic waste film can be used to produce silver nanoparticles in situ in a manner which is environmentally benign ("green"). Further, laser ablation can form smaller particles stabilized by the amine pendant groups on the gelatin backbone, which leads to the formation of gelatin-stabilized silver nanoparticles. The following examples will further illustrate the process of making silver nanoparticles.

Materials

Fuji medical X-ray waste film having a silver content of 5 g/m² was used as the starting recycled material. Glucose, polyvinylpyrrolidone (PVP) having a molecular weight 40000 g/mol, ammonia solution 25% $NH_3$ and sodium hydroxide (NaOH) were all used without purification. X-ray powder diffraction (XRD) patterns were recorded using a D/max 2550 V X-ray diffractometer. Transmission electron microscopy (TEM) micrographs were taken with a JEOL JEM-2100F. Ultraviolet visible (UV-vis) absorption spectra were obtained with a Techcomp UV2300 spectrophotometer. The synthetic stomach fluid was prepared according to well established methods, using deionized distilled (DDI) water, HCl (0.42 M) and glycine (0.40 M) pH 1.5.

Example 1

Synthesis of Silver Nanoparticles Using Ammonia Solution

The waste X-ray films were cut into small pieces and about 10 g of these cut pieces were weighed and mixed with 90 mL of 25% of ammonia ($NH_3$) solution and heated at 50° C. for 1 hour until the color of the solution was converted from colorless to blue. The solid film pieces were filtered. The solution was subjected to ultracentrifugation at 21,0000 rpm.

Example 2

Synthesis of Silver Nanoparticles Using NaOH Solution

The waste X-ray films were cut into small pieces and about 10 g was weighed and mixed with 90 mL of 1 M NaOH solution and heated at 70° C. for 1 hour until the color of the solution was converted from blue to dark red. The solid film pieces were filtered and the solution was subjected to ultracentrifugation at 21,0000 rpm.

Figure 4:
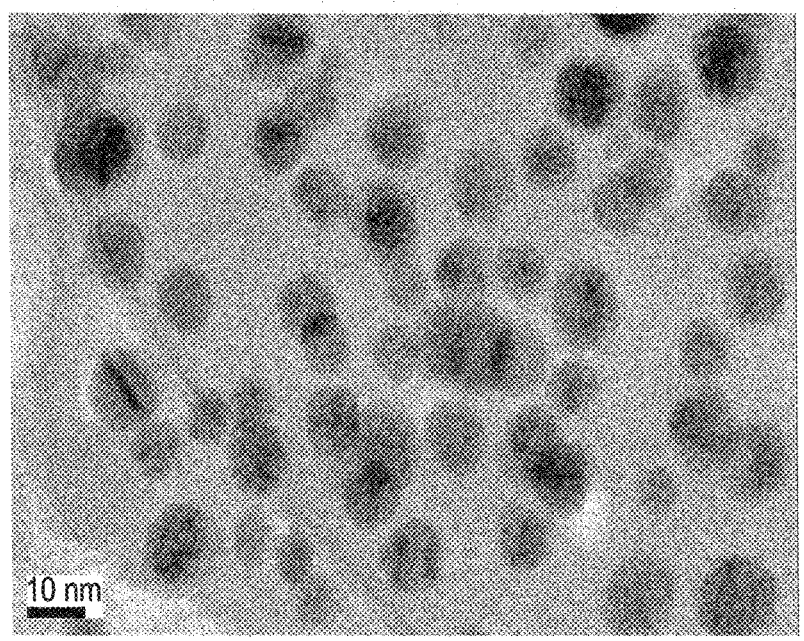
FIG. 4 shows the Transmission Electron Micrograph (TEM) of product obtained by the method of Example 2.

The UV-Vis spectrum of the silver nanoparticles is represented in FIG. 1. The blue shift and narrow distribution of the UV-Vis spectrum at 405 nm indicated the formation of silver nanoparticles with small size. The nanoparticles are relatively monodispersed in size. FIG. 4 shows the Transmission Electron Micrograph (TEM) results.

Example 3

Synthesis of Silver Nanoparticles Using Ammonia Solution with Glucose

Figure 5:
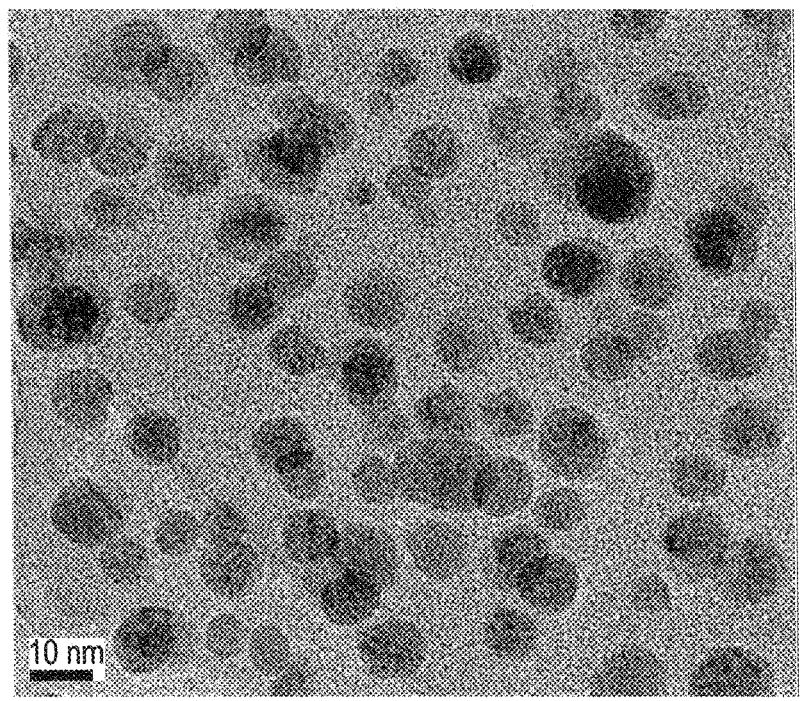
FIG. 5 shows the TEM of product obtained by the method of Example 3.

The waste X-ray films were cut into small pieces and about 10 g was weighed and mixed with 90 mL of 25% of ammonia solution and heated at 60° C. for 1 hour until the color of solution converted from blue to dark red. Then, 10 mL of an aqueous glucose solution containing 4 g of glucose was added to the reaction mixture. The temperature was raised up slowly up to 90° C. during a period of 1 hour. The red color of reaction mixture converted to black. The solid film pieces were filtered. The solution was subjected to ultracentrifugation at 21,0000 rpm. FIG. 5 shows the TEM of the product.

Example 4

Synthesis of Silver Nanoparticles Using NaOH Solution with Glucose

Figure 2:
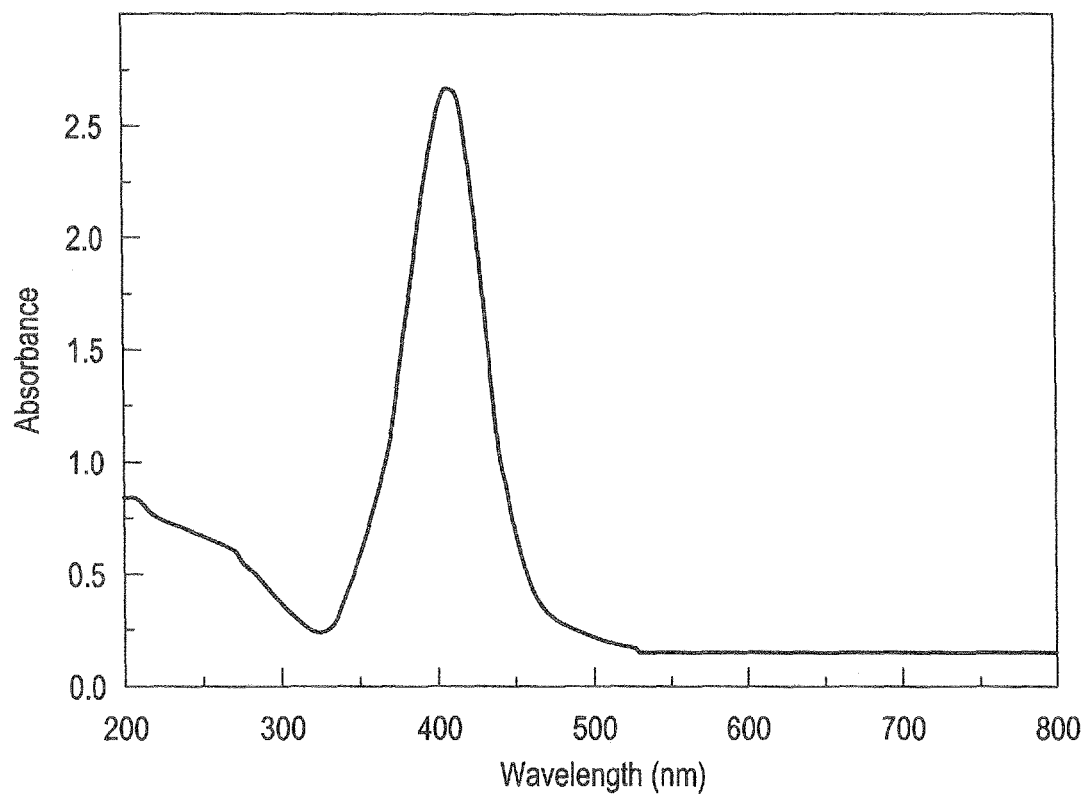
FIG. 2 shows the UV-Vis spectrum of product obtained by the method of Example 4.
Figure 6:
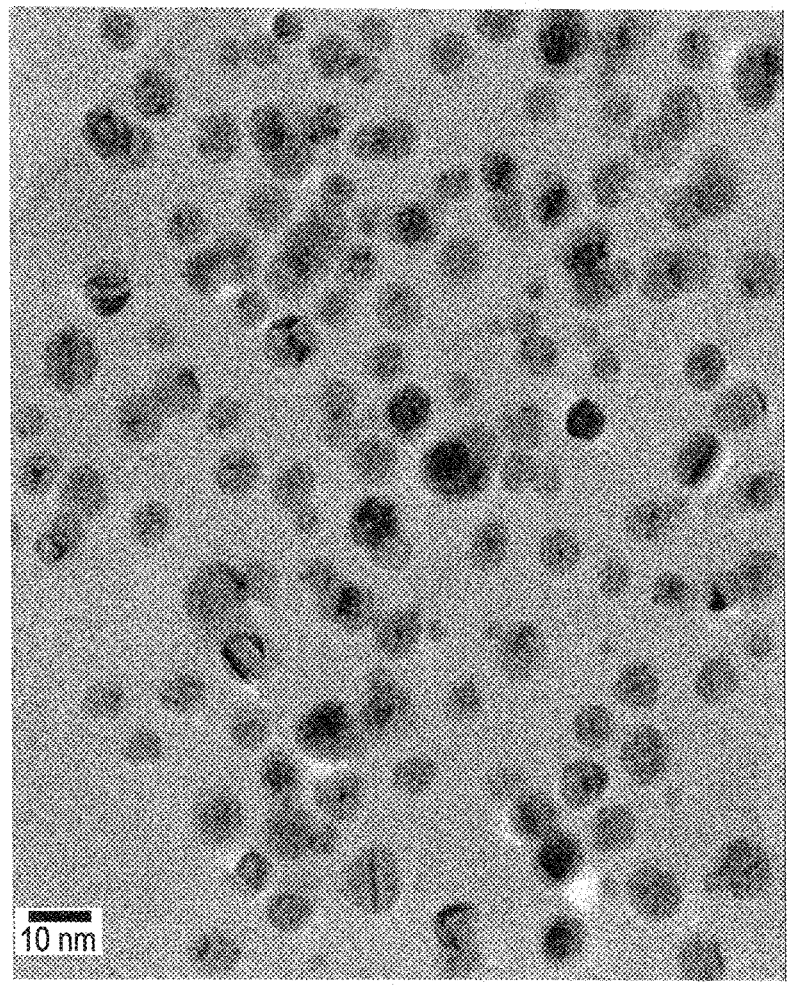
FIG. 6 shows the TEM of product obtained by the method of Example 4.

The waste X-ray films were cut into small pieces and about 10 g were weighed and mixed with 90 mL of 1 M NaOH and heated at 50° C. for 1 hour until the color of the solution was converted from blue to dark red. Then, 10 mL of an aqueous glucose solution containing 4 g of glucose was added to the reaction mixture. The temperature was raised up slowly up to 70° C. during a period of 1 hour. The red color of reaction mixture was converted to black. The solid film pieces were filtered. The solution was subjected to ultracentrifugation at 21,0000 rpm. As shown in FIG. 2, the intensity of the UV-visible spectra increased with the use of glucose as a reducing agent. FIG. 6 shows the TEM of the product.

Example 5

Synthesis of Silver Nanoparticles Using Ammonia Solution with PVP

Figure 7:
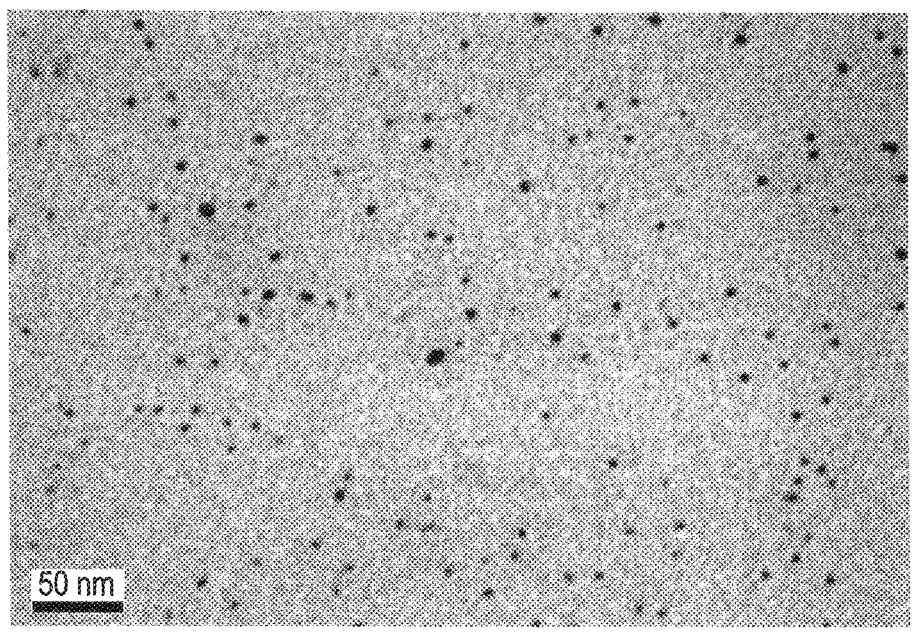
FIG. 7 shows the TEM of product obtained by the method of Example 5.

In this method, X-ray film pieces (about 10 g) were introduced into the reaction bath after heating 90 mL of 25% of ammonia solution with PVP (2 g), which was set at 60° C. within 60 min. Then, the temperature was gradually raised up to a boiling point within 60 min and the treatment was continued for another 60 minutes. The red color of reaction mixture was converted to black. The solid film pieces were filtered. The solution was subjected to ultracentrifugation at 21,0000 rpm. FIG. 7 shows the TEM of the product.

Example 6

Synthesis of Silver Nanoparticles Using NaOH Solution with PVP

Figure 3:
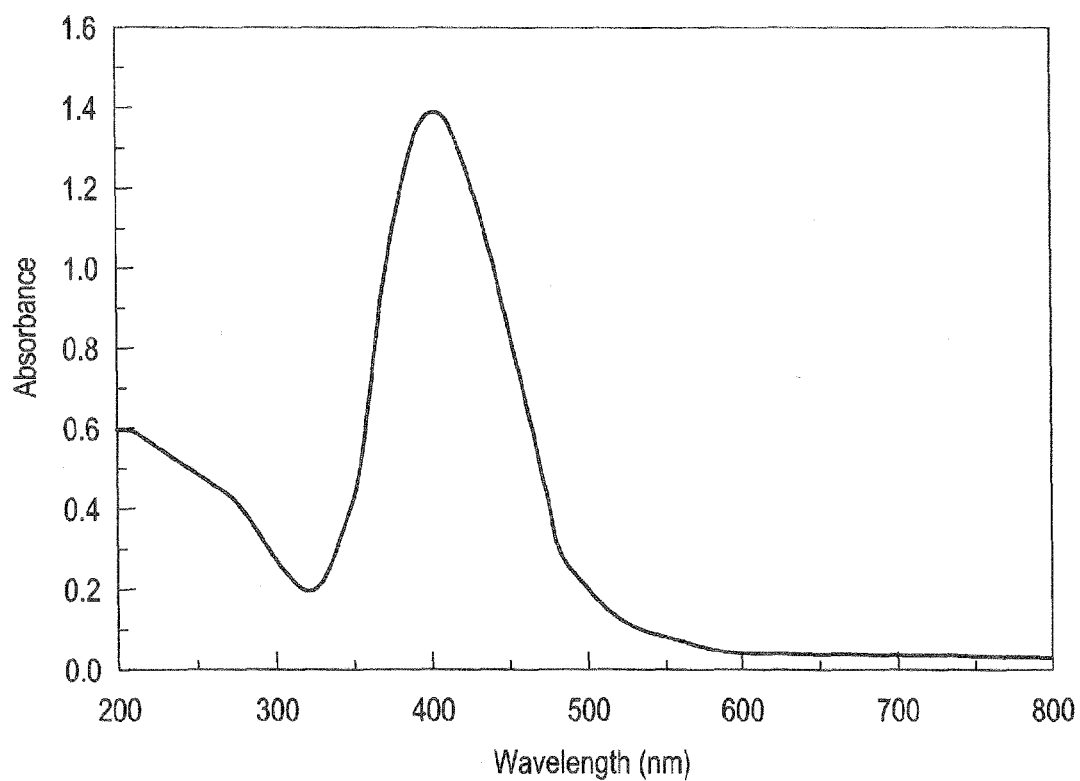
FIG. 3 shows the UV-Vis spectrum of product obtained by the method of Example 5.
Figure 8:
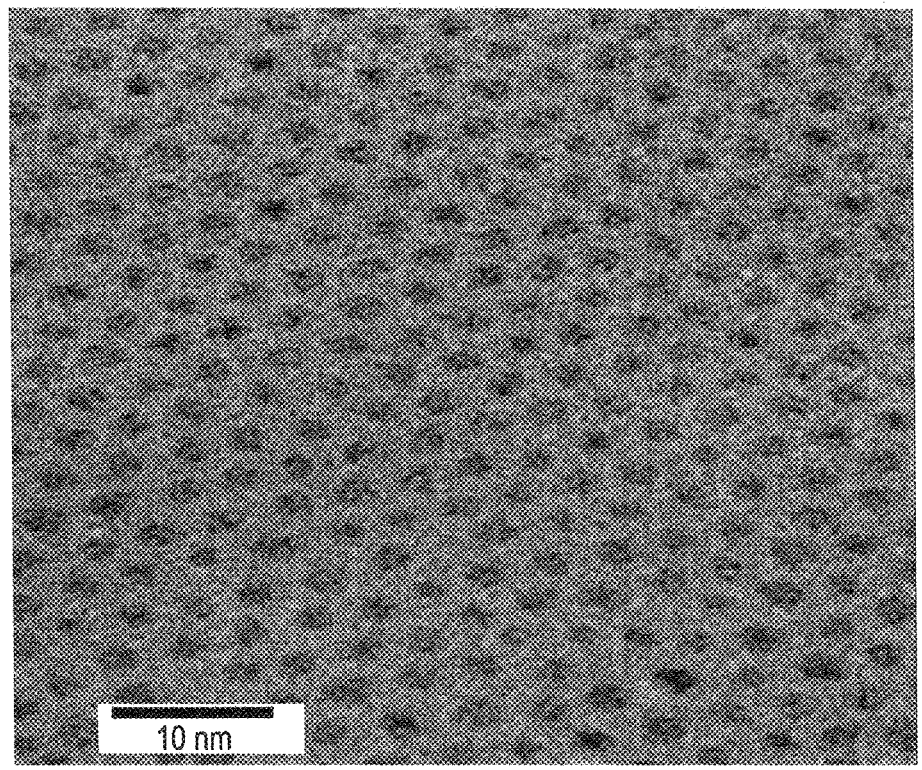
FIG. 8 shows the TEM of product obtained by the method of Example 6.
Figure 9:
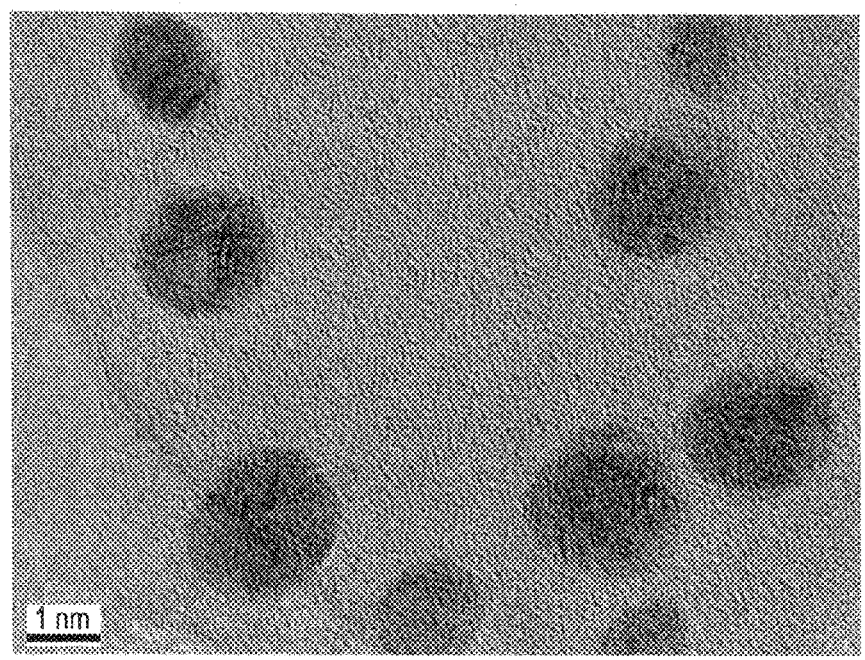
FIG. 9 shows the TEM (high resolution) of silver nanoparticles obtained by the method of Example 6.
Figure 10:
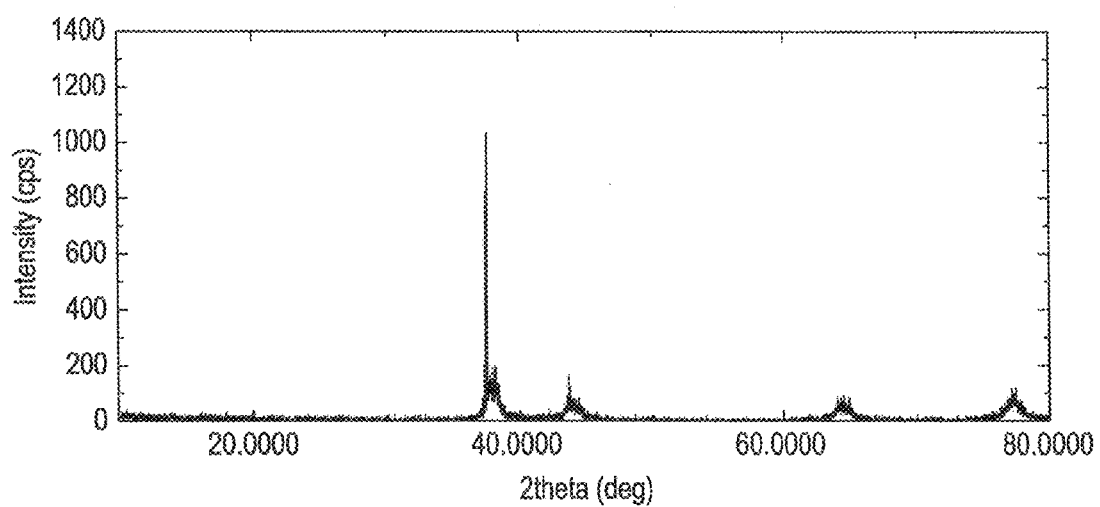
FIG. 10 shows the X-ray powder diffraction (XRD) pattern of nanoparticles obtained by the method of Example 6.

In this method, X-ray film pieces (about 10 g) were introduced into the bath after heating 90 mL (1 M NaOH) with PVP (about 2 g), which was at 60° C. within 60 min. Then the temperature was gradually raised up to boiling point within 60 min and the treatment was continued for another 60 min. The red color of reaction mixture was converted to black. The solid film pieces were then filtered and the solution was subjected to ultracentrifugation at 21 0000 rpm. The silver nanoparticles had an average particle size of about 2.7 nm. The silver nanoparticles were monodisperse. As shown in FIG. 3, the narrow distribution of the UV-Vis spectrum increased with the use of PVP as a stabilizer. FIG. 8 shows the TEM of the silver nanoparticles. FIG. 9 shows the TEM (high resolution) of the silver nanoparticles. FIG. 10 shows the X-ray powder diffraction (XRD) pattern of the nanoparticles. The XRD pattern in FIG. 10 shows that the product prepared by all methods consisted of metallic Ag with a cubic structure. The broadening of peaks indicates very small sizes of Ag crystallites.

Example 7

Stability to Stomach Synthetic Fluid

Figure 11:
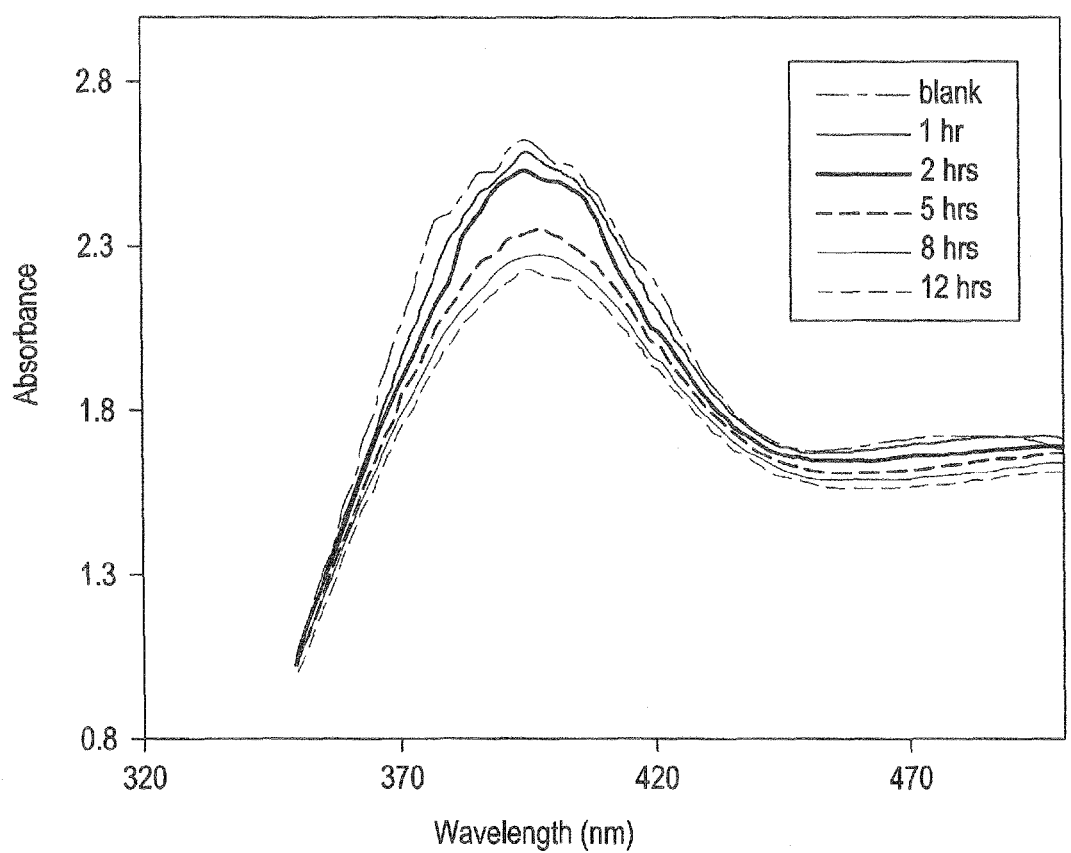
FIG. 11 shows the UV-Vis spectra of silver nanoparticles produced by the method of Example 6 in synthetic stomach fluid at different time intervals.

Silver nanoparticles made in accordance with the method described in Example 6, were suspended in 0.5M aqueous HCl and 0.4M glycine conditions. FIG. 11 shows the UV-vis absorption spectra acquired with time under 0.5M aqueous HCl and 0.4 M glycine conditions. The absorption peak of silver nanoparticles decreased without blue or red shift and the broadness increased after 1 hour. This may be caused by a gradual increase in the average particle diameter due to the Ostwald ripening process. However, the coating on the nanoparticles clearly has a strong effect on their stability.

Example 8

Corrosion Inhibition in 1M HCl

Figure 12:
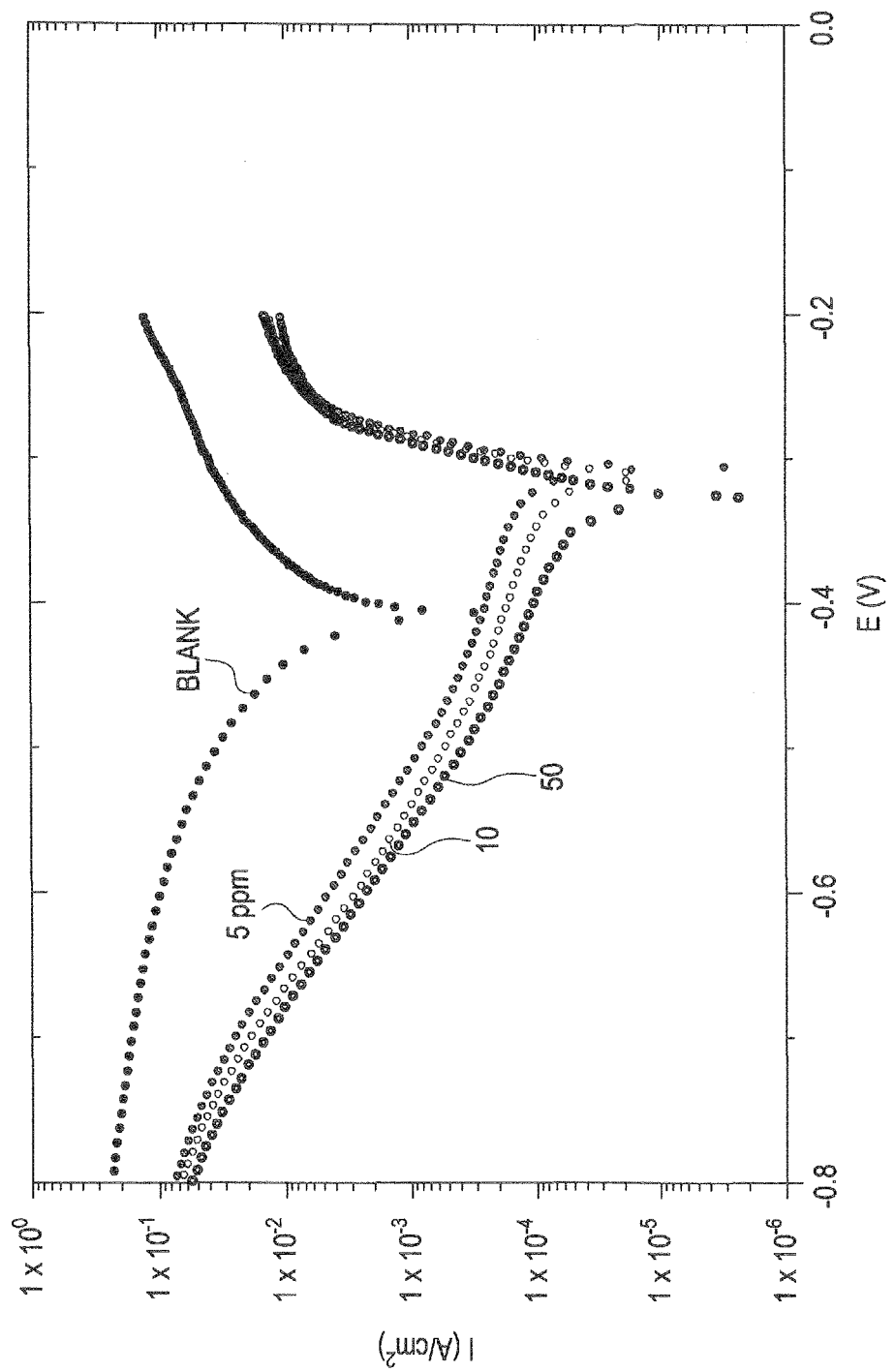
FIG. 12 shows the electrochemical polarization of silver nanoparticles prepared by method of Example 5 for steel in 1M HCl.

The influence of various concentrations of silver nanoparticles prepared by method of Example 5 on the polarization behavior of carbon steel (CS) in 1M HCl solution is shown in FIG. 12. The data indicate that the presence of silver nanoparticles shifts the anodic curves to more positive potentials and the cathodic curves to more negative potentials and to lower values of current densities. Both anodic and cathodic reactions are drastically inhibited. The results can be attributed to the adsorption of silver nanoparticles on both anodic and cathodic reactive sites, which inhibited the anodic and cathodic reactions of carbon steel corrosion. The inhibition efficiencies for different inhibitor concentrations were calculated from the following equation:

$$IE(\%) = i_{corr}^{\circ} - i_{corr}/i_{corr}^{\circ} \qquad (2)$$

where $i_{corr}^{\circ}$ and $i_{corr}$ are the corrosion current densities for carbon steel electrode in the uninhibited and inhibited solutions, respectively. The IE % was calculated and quoted in Table 1. It can be seen from the data presented in Table 1 that inhibition efficiency achieved good results at low concentration 10 ppm. The results indicate the formation of thin film and good stability of silver nanoparticles to 1 M HCl which prevents the formation of silver ions or conversion of silver nanoparticles to silver chloride. It is clear from the obtained corrosion data that, the Tafel lines shifted towards more negative and more positive potentials during the anodic and cathodic processes, respectively, relative to the blank curve. It can be concluded that silver nanoparticles prepared by method 5 acted as a mixed type of inhibitor.

Figure 13:
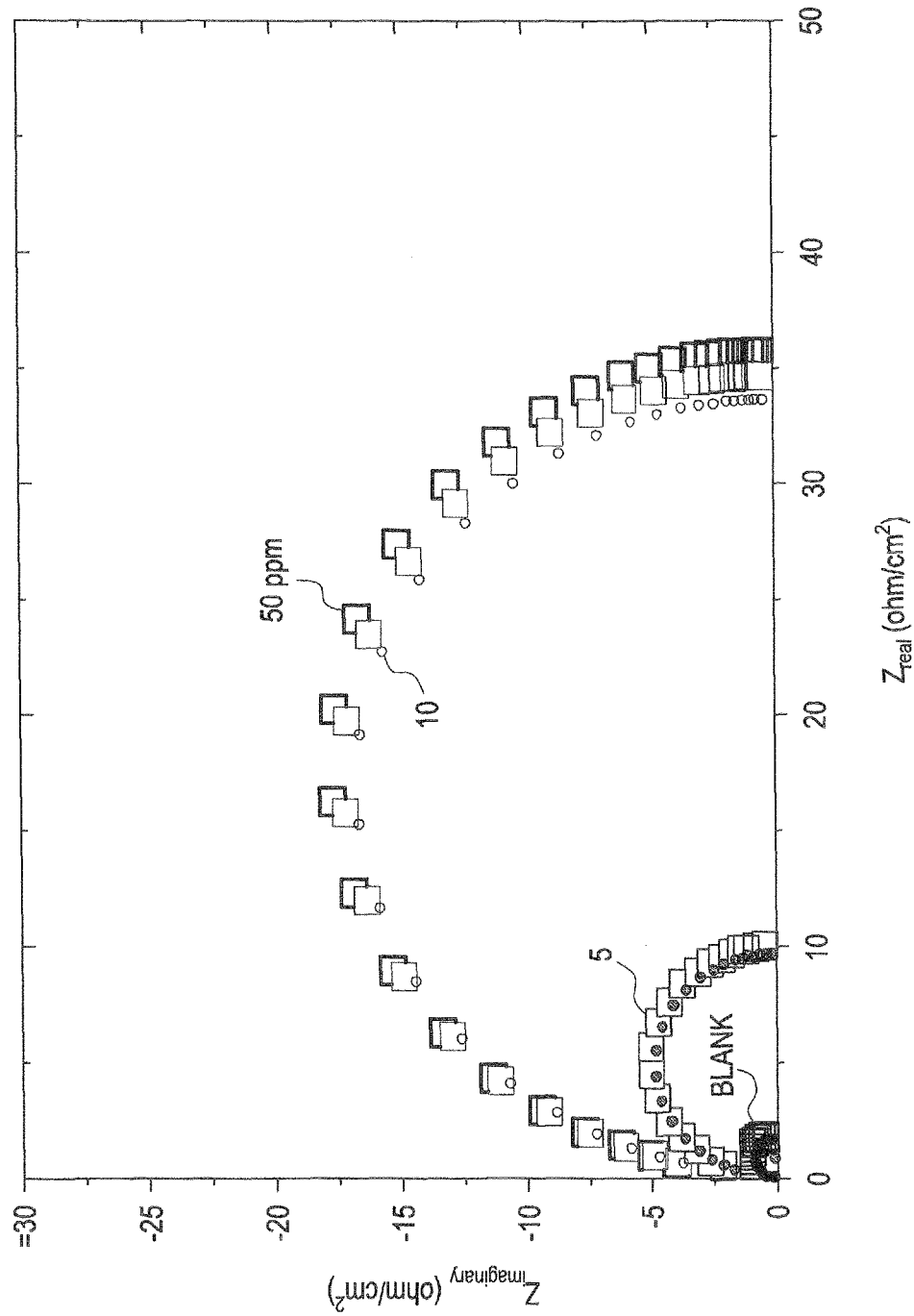
FIG. 13 shows impedance of silver nanoparticles produced by the method of Example 5 for steel in 1M HCl.

This behavior was elucidated by electrochemical impedance measurement as illustrated in FIG. 13. Nyquist diagrams of silver nanoparticles prepared by method 5 in 1 M HCl without and with different inhibitor concentrations (5-50 ppm) of silver nanoparticles prepared by method 5. All the impedance spectra exhibit one single semicircle. The inhibition efficiency (IE) is calculated from:

$$IE\% = (1 - R_{ct}/R^*_{ct}) \times 100 \quad (3)$$

where $R^*_{ct}$ and $R_{ct}$ are the charge-transfer resistances with and without inhibitors, respectively. IE % was calculated and presented in Table 1. Table 1 shows the inhibition efficiency values for steel in 1M HCl with different concentrations of silver nanoparticles prepared by the method of Example 5, calculated by Polarization and EIS methods. The inhibition efficiencies calculated from EIS are in good agreement with those obtained from potentiodynamic polarization curves.

TABLE 1

| | Polarization Method | | | | | EIS Method | | |
|---|---|---|---|---|---|---|---|---|
| | Ba (mV) | Bc (mV) | $E_{corr}$ (V) | $i_{corr}$ μA/cm² | IE % | $R_p$ Ohm | Cdl (μF/cm²) | IE % |
| Blank | 69 | 120 | −0.3955 | 839 | — | 1.80 | 334 | — |
| 5 ppm | 50 | 394 | −0.3061 | 152 | 81.8 | 10.1 | 137 | 82.1 |
| 10 | 41 | 173 | −0.3139 | 49 | 94.1 | 35 | 106 | 94.8 |
| 50 | 46 | 195 | −0.3282 | 44 | 94.7 | 36 | 104 | 95.0 |

Example 9

Antimicrobial Activity of Silver Nanoparticles Prepared by the Methods of Examples 5 and 6

Antimicrobial effects and minimum inhibitory concentration (MIC) and minimum bactericidal concentration (MBC) of the silver nanoparticles prepared by samples 5 and 6 were determined using the broth-micro dilution test against three common strains of bacteria; *Escherichia coli* ATCC 8739, *Staphylococcus aureus* ATCC 6538, *Bacillus subtilis* ATCC 6633 and *Pseudomonas aeruginosa* ATCC 10145. Stock culture (0.1 mL) containing approximately 10×10⁶ CFU mL⁻¹ of each bacterial suspension and ~2.5-100 mg of sterile samples were inoculated in 9.9 mL nutrient broth. Incubation was carried out at 35° C. for 18-24 h. For enumeration, the cultures in each media were serially diluted 10×10⁵ fold using sterile FTS solution, and 100 μL of each diluted sample was placed on nutrient agar and incubated for 18-24 h at 35° C., and finally, the colonies were counted. The minimum inhibitory concentration (MIC; μg mL⁻¹) of magnetite coated nanoparticles using different types of gram positive (*Staphylococcus aureus* ATCC 6538 and *Bacillus subtilis* ATCC 6633) and negative (*Escherichia coli* ATCC 8739 and *Pseudomonas aeruginosa* ATCC 10145) bacterial strains were determined and listed in Tables 2 and 3 respectively. The data indicated that silver nanoparticles prepared by method 5 and 6 achieved good results with all tested bacterial strains. In the present work, the stability of silver nanoparticles enhanced antimicrobial activity of the resultant nanoparticles and completely inhibited growth as MIC was achieved.

Table 2 shows the minimum inhibition concentration (MIC) and the percentage (%) reduction of organism for 10, 5, 2.5, and 1 μg mL⁻¹ of samples against *Escherichia coli* ATCC 8739, *Staphylococcus aureus* ATCC 6538, *Bacillus subtilis* ATCC 6633, and *Pseudomonas aeruginosa* ATCC 10145 strains using silver nanoparticles prepared by the method of Example 5.

TABLE 2

| Anti-microbial Materials | MBC (mg mL⁻¹) | MIC (mg mL⁻¹) | The reduction of organism (%) | | | |
|---|---|---|---|---|---|---|
| | | | 1 μg mL⁻¹ | 2.5 μg mL⁻¹ | 5 μg mL⁻¹ | 10 μg mL⁻¹ |
| *E. coli*− | 10 | <10 | — | — | 41 ± 4 | 100 |
| *S. aureus*+ | 10 | 2.5 | 53 ± 9 | 98 ± 0.2 | 99 ± 0.3 | 100 |
| *B. subtilis*+ | — | 2.5 | 66 ± 4 | 90 ± 1 | 94 ± 2 | 97 ± 2 |
| *P. aeruginosa*− | — | 10 | 31 ± 8 | 59 ± 3 | 75 ± 8 | 97 ± 2 |

Table 3 shows the Minimum inhibition concentration (MIC) and the % reduction of organism for 10, 5, 2.5, and 1 μg mL⁻¹ of samples against *Escherichia coli* ATCC 8739, *Staphylococcus aureus* ATCC 6538, *Bacillus subtilis* ATCC 6633, *Pseudomonas aeruginosa* ATCC 10145 strains using silver nanoparticles prepared by method of Example 6.

TABLE 3

| Anti-microbial materials | MBC (μg mL⁻¹) | MIC (μg mL⁻¹) | The Reduction of Organism (%) | | | |
|---|---|---|---|---|---|---|
| | | | 1 μg mL⁻¹ | 2.5 μg mL⁻¹ | 5 μg mL⁻¹ | 10 μg mL⁻¹ |
| *E. coli*− | — | 10 | 40 ± 12 | 55 ± 4 | 70 ± 7 | 89 ± 3 |
| *S. aureus*+ | — | 1 | 90 ± 6 | 94 ± 4 | 98 ± 1 | 98 ± 1 |
| *B. subtilis*+ | 10 | 2.5 | 40 ± 15 | 97 ± 3 | 99 ± 0.4 | 100 |
| *P. aeruginosa*− | 5 | 2.5 | 74 ± 4 | 98 ± 1 | 100 | 100 |

It is to be understood that the present invention is not limited to the embodiments described above, but encompasses any and all embodiments within the scope of the following claims.

We claim:

1. A method of synthesizing silver nanoparticles from waste film comprises:
   providing waste film including a silver halide salt and gelatin;
   mixing the waste film with an alkaline solution to form a mixture;
   heating the mixture to a temperature of about 50° C. to about 70° C.; and
   adding a glucose solution to the mixture after heating the mixture to a temperature of about 50° C. to about 70° C.

2. The method of synthesizing silver nanoparticles according to claim 1, further comprising subjecting the mixture including the glucose solution to ultracentrifugation to isolate silver nanoparticles in the mixture.

3. The method of synthesizing silver nanoparticles according to claim 1, further comprising heating the mixture to a temperature of about 70° C. to about 90° C. after adding the glucose solution to the mixture.

4. The method of synthesizing silver nanoparticles according to claim 1, wherein the alkaline solution includes sodium hydroxide (NaOH) or ammonia.

5. The method of synthesizing silver nanoparticles according to claim 4, wherein the mixture further includes poly vinyl pyrrolidone (PVP).

6. The method of synthesizing silver nanoparticles according to claim 5, further comprising heating the mixture to its boiling point after heating the mixture to a temperature of about 50° C. to about 70° C.

7. The method of synthesizing silver nanoparticles according to claim 1, wherein the waste film includes waste radiographic or photographic film pieces.

8. The method of synthesizing silver nanoparticles according to claim 7, wherein the radiographic film pieces include medical X-ray film pieces.

9. The method of synthesizing silver nanoparticles according to claim 1, wherein the silver nanoparticles are about 2 nm to about 10 nm in size.

10. The method of synthesizing silver nanoparticles according to claim 1, wherein the silver nanoparticles are monodisperse.

11. A method of synthesizing silver nanoparticles from waste film comprises:
    providing waste film including a silver halide salt and gelatin;
    mixing the waste film with an alkaline solution to form a mixture;
    heating the mixture to a temperature of about 50° C. to about 70° C.; and
    subjecting the mixture to ultracentrifugation to isolate silver nanoparticles in the mixture.

12. The method of synthesizing silver nanoparticles according to claim 11, further comprising adding a glucose solution to the mixture after heating the mixture to a temperature of about 50° C. to about 70° C.

13. The method of synthesizing silver nanoparticles according to claim 12, further comprising heating the mixture to a temperature of about 70° C. to about 90° C. after adding the glucose solution to the mixture.

14. The method of synthesizing silver nanoparticles according to claim 11, wherein the alkaline solution includes sodium hydroxide (NaOH).

15. The method of synthesizing silver nanoparticles according to claim 14, wherein the mixture further includes poly vinyl pyrrolidone (PVP).

16. The method of synthesizing silver nanoparticles according to claim 15, further comprising heating the mixture to boiling point after heating the mixture to a temperature of about 50° C. to about 70° C.

17. The method of synthesizing silver nanoparticles according to claim 11, wherein the waste film includes waste radiographic or photographic film pieces.

18. The method of synthesizing silver nanoparticles according to claim 17, wherein the radiographic film pieces include medical X-ray film pieces.

19. The method of synthesizing silver nanoparticles according to claim 11, wherein the silver nanoparticles are about 2 nm to about 10 nm in size.

20. The method of synthesizing silver nanoparticles according to claim 11, wherein the silver nanoparticles are monodisperse.

\* \* \* \* \*